(12) United States Patent
Spahn

(10) Patent No.: US 7,635,221 B2
(45) Date of Patent: Dec. 22, 2009

(54) MECHANICALLY FLEXIBLE X-RAY IMAGING SYSTEM

(75) Inventor: Martin Spahn, Erlangen (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 12/325,663

(22) Filed: Dec. 1, 2008

(65) Prior Publication Data

US 2009/0180595 A1  Jul. 16, 2009

Related U.S. Application Data

(60) Provisional application No. 61/020,485, filed on Jan. 11, 2008.

(51) Int. Cl.
*H05G 1/06* (2006.01)

(52) U.S. Cl. ...................... 378/194; 378/197

(58) Field of Classification Search ......... 378/193–198, 378/4–20
See application file for complete search history.

(56) References Cited

U.S. PATENT DOCUMENTS

| | | |
|---|---|---|
| 4,805,202 A | 2/1989 | Deucher et al. |
| 5,631,943 A | 5/1997 | Miles |
| 5,781,610 A | 7/1998 | Miles |
| 6,038,287 A | 3/2000 | Miles |
| 2002/0085682 A1* | 7/2002 | Noegel et al. ............... 378/198 |
| 2005/0053199 A1 | 3/2005 | Miles |

* cited by examiner

*Primary Examiner*—Hoon Song

(57) ABSTRACT

An X-ray imaging system includes a joint enabling rotation of an X-ray device rotatable arm unrestricted by cabling. An X-ray imaging system usable in medical interventional procedures includes a rotatable arm. A rotatable arm includes an X-ray radiation emitting device located towards one end of the rotatable arm and an X-ray detector device located towards the opposite end of the rotatable arm. The detector device acquires X-ray radiation emitted by the emitting device that has passed through a patient. A base unit supports the rotatable arm and includes a joint enabling rotation of the rotatable arm unrestricted by cabling, about a patient on a support surface. The joint includes, (a) mating electrical contact surfaces providing electrical power to the rotatable arm from the base unit during rotation of the rotatable arm unrestricted by cabling and (b) a signal interface for providing electrical signals received from the rotatable arm to the base unit during rotation of the rotatable arm unrestricted by cabling. An X-ray imaging system controller controls application of electrical power to the rotatable arm via the base unit.

18 Claims, 7 Drawing Sheets

MECHANICALLY FLEXIBLE X-RAY IMAGING SYSTEM

This is a non-provisional application of provisional application Ser. No. 61/020,485 filed Jan. 11, 2008, by M. Spahn.

FIELD OF THE INVENTION

This invention concerns an X-ray imaging system usable in medical interventional procedures, comprising a rotatable arm, supporting an X-ray radiation emitting device and being movable about a patient on a support surface unrestricted by cabling.

BACKGROUND OF THE INVENTION

Known interventional X-ray systems use a movable arm such as a C-arm, to support an X-ray emitter and a detector. A C-arm may be floor-mounted or ceiling mounted. A C-arm may also be mounted on a robotic stand to provide flexible, automated arm manipulation. An X-ray detector and emitter, as well as motor drives require electrical power, electronic data and control signals to be provided via cables and may also require coolant connections if a detector requires cooling, for example. Electrical cables and wires as well as cooling tubes are usually incorporated within a thick support cable housing or tube. Due to the support cable, the degrees of freedom of the C-arm or robotic stand are limited. In X-ray image acquisition of a three dimensional (3D) anatomical volume, C-arm movement may be limited to between 180 and 360 degrees of C-arm rotation, for example. Continuous rotation, involved in spiral-CT (Computerized Tomography) is not possible for interventional systems constrained by a support cable. Also, X-ray mask and content (non-mask) imaging acquisitions require a C-arm to be moved back and forth, which requires more time than an alternative continuous rotation (with mask and content image acquisitions occurring successively) and this is more prone to introduction of motion artifacts due to patient movement. A system according to invention principles addresses these deficiencies and related problems.

SUMMARY OF THE INVENTION

Known interventional X-ray imaging systems including C-arm and robotic systems, use an external cable to provide high voltage to an X-ray emission tube as well as electrical and possibly cooling connections to an X-ray detector. The cable limits the degrees of freedom of the C-arm. An X-ray imaging system includes a joint enabling rotation of a rotatable arm unrestricted by cabling using contact rings, wireless data transmission and detectors which do not require external cooling, enabling spiral CT type movement of a C-arm possible, for example. An X-ray imaging system usable in medical interventional procedures includes a rotatable arm. A rotatable arm includes an X-ray radiation emitting device located towards one end of the rotatable arm and an X-ray detector device located towards the opposite end of the rotatable arm. The detector device acquires X-ray radiation emitted by the emitting device that has passed through a patient. A base unit supports the rotatable arm and includes a joint enabling rotation of the rotatable arm unrestricted by cabling, about a patient on a support surface. The joint includes, (a) mating electrical contact surfaces providing electrical power to the rotatable arm from the base unit during rotation of the rotatable arm unrestricted by cabling and (b) a signal interface for providing electrical signals received from the rotatable arm to the base unit during rotation of the rotatable arm unrestricted by cabling. An X-ray imaging system controller controls application of electrical power to the rotatable arm via the base unit.

DETAILED DESCRIPTION OF THE INVENTION

Figure 1:
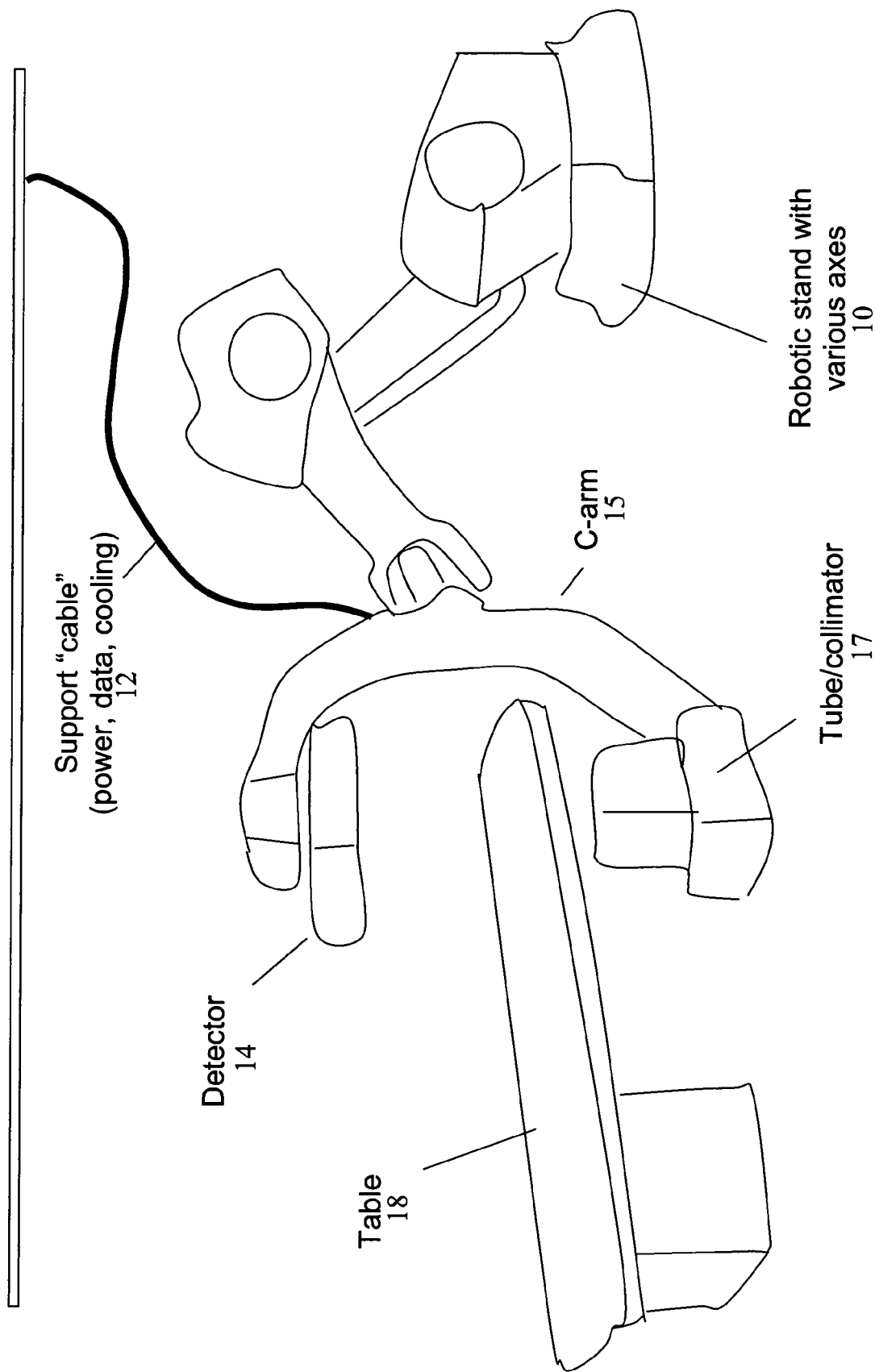
FIGS. 1 and 2 show known X-ray imaging systems involving support cabling.

An X-ray imaging system comprises a robotic base unit supporting a rotatable arm via a joint enabling rotation of the arm unrestricted by cabling. The system overcomes mechanical restrictions imposed on movement of a movable X-ray imaging system arm by external cabling and enables X-ray imaging to be performed on larger anatomical volumes in a continuous motion or rotation. The system eliminates support cabling using a joint including, mating electrical contact surfaces providing electrical power and signals to a rotatable arm from a base unit during rotation of the arm unrestricted by cabling. In one embodiment, a joint conveys high voltage (e.g., for X-ray emission tube) and low voltage (e.g., for an X-ray detector, motor drives) via contact rings. Alternatively, high voltage generation is integrated into a C-arm, so that only relatively low voltage needs to be supported via contact rings. The contact rings (or segments) may comprise metal (for example Copper), isolated from surroundings on one side of the joint (also comprising a pivot) and brushes (carbon or graphite brushes) on the other side.

In one embodiment, low voltages (low relative to the high voltage used for X-ray emission) are conveyed in the joint via contact rings and used to power an X-ray detector, a collimator, a dose meter, other subsystems requiring power which are mounted on the arm and various motors for moving the robotic arm, rotation of the collimator and detector on the arm and SID (source-imager-distance) movement, for example. In an alternative embodiment, the relatively low voltages or signals are conveyed via contact-less capacitive coupling in the joint. Further, X-ray image detector image data and control signals may be conveyed in a joint by different arrangements including, contact rings, a wireless interface (such as a Wi-Fi link, WIMAX or other broadband local point-to-point network), contact-less optical interface (e.g., an opto-isolator) and contact-less capacitive coupling. In order to eliminate cooling related cabling, the system employs an X-ray detector that does not need cooling or if it does require cooling, the detector uses air-cooling (such as a fan) or otherwise the cooling unit (water or other fluid) is directly integrated into the arm. Also the arm may have integrated cooling fins to divert heat into the surrounding air. The different methods used to eliminate external cabling may be combined in a variety of different combinations.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof. A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. An object or data object comprises a grouping of data, executable instructions or a combination of both or an executable procedure.

Figure 2:
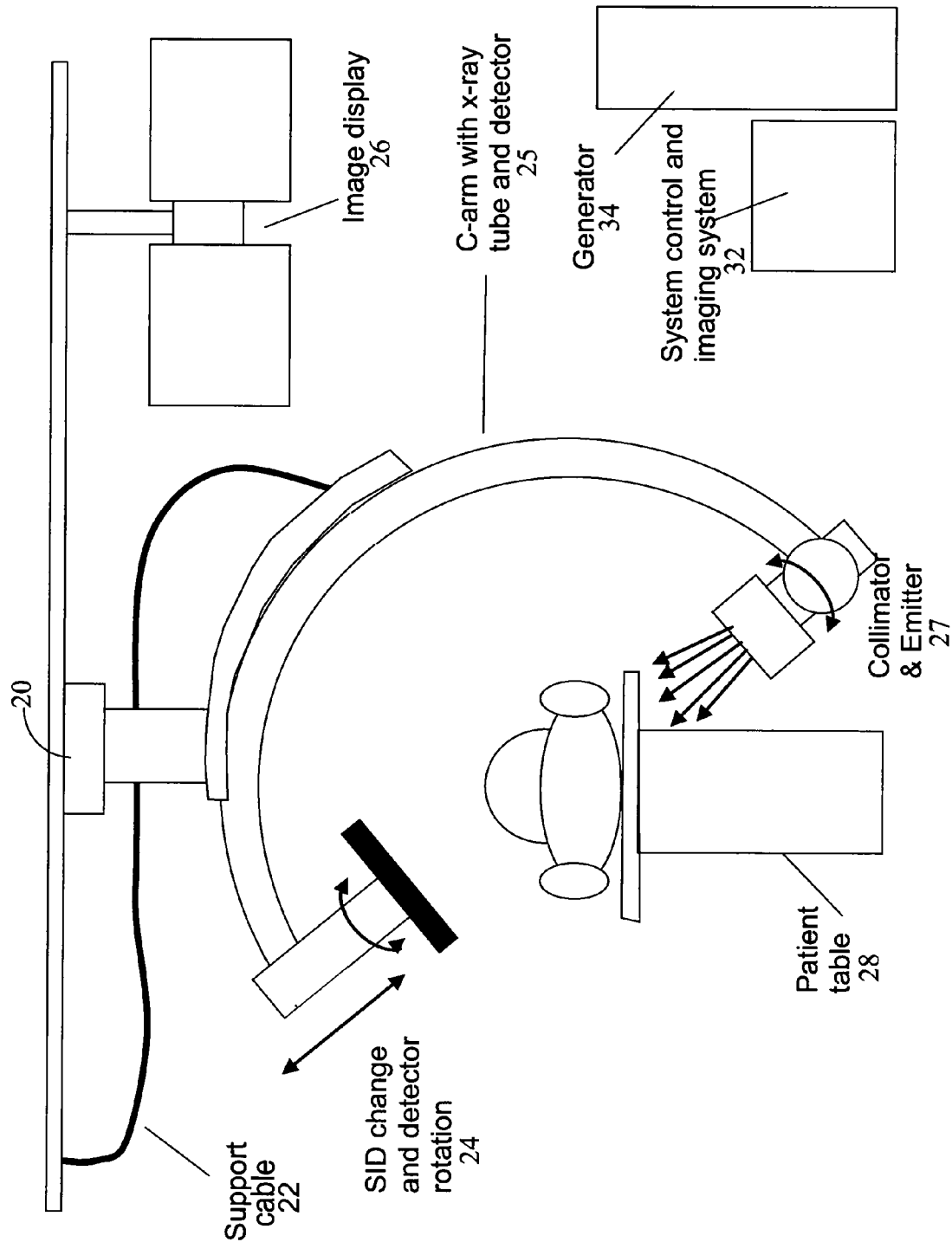

FIGS. 1 and 2 show known X-ray imaging systems involving support cabling. FIG. 1 shows robotic stand 10 and support cable 12 powering X-ray detector 14 and X-ray tube and collimator 17 mounted on C-arm 15 as well as mechanical drives. Cable 12 also conveys data and control signals and possibly includes a cooling tube conveying coolant for detector 14. The system performs interventional angiography and two dimensional and three dimensional (2D and 3D) image data acquisition for a patient on table 18.

FIG. 2 shows a ceiling mount 20 C-arm interventional X-ray imaging system with support cable 22 powering X-ray detector and SID (source-imager-distance) drive 24 and X-ray emission tube and collimator 27 mounted on C-arm 25 as well as mechanical drives for SID, detector and collimator rotation. Generator 34 provides the electrical power conveyed via cable 22. Cable 22 also conveys data and control signals and may include a cooling tube conveying coolant for detector 14. The system performs interventional angiography and two dimensional and three dimensional (2D and 3D) image data acquisition for a patient on table 28. User interface 26 presents medical images and the system is controlled by system imaging control unit 32.

Figure 3:
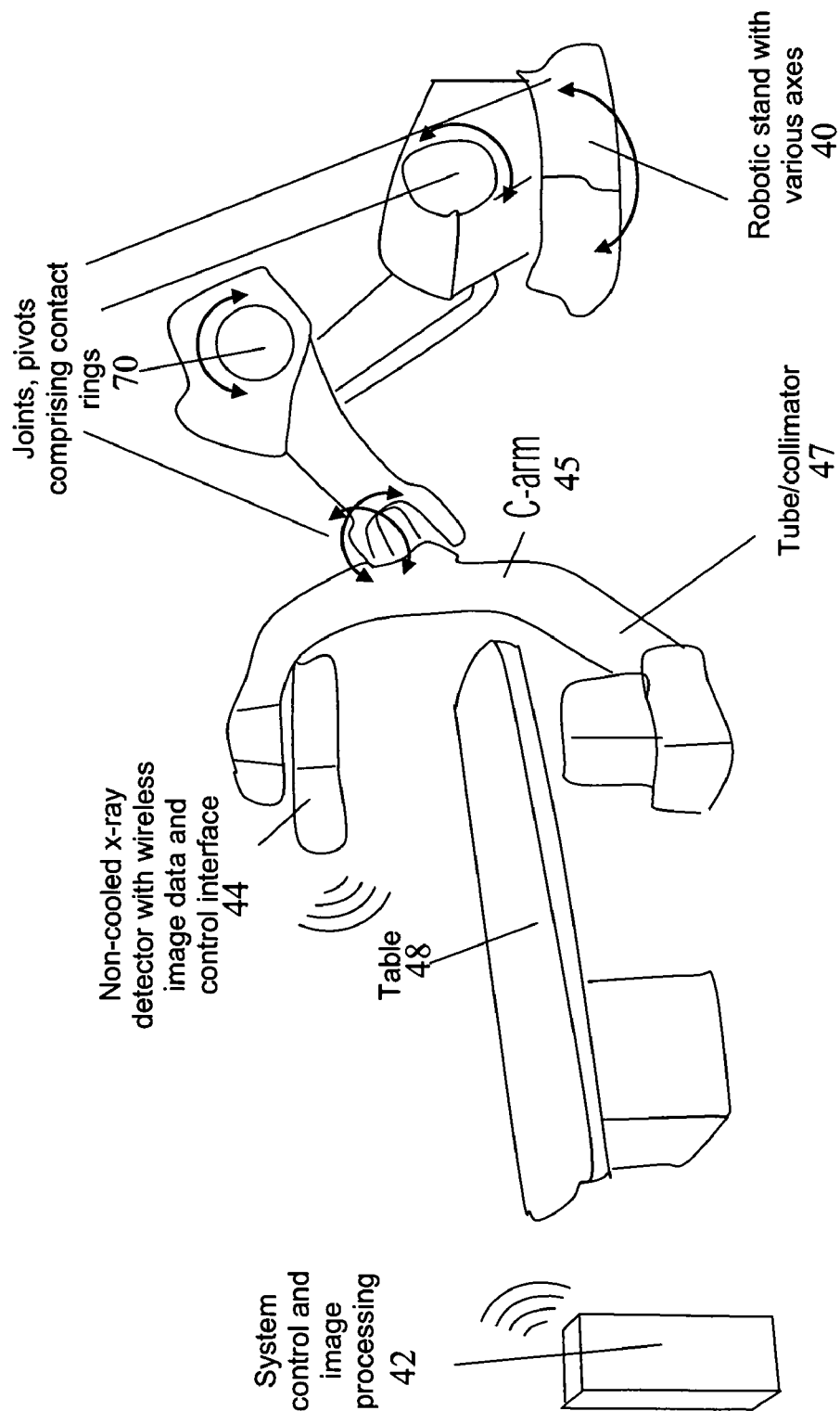
FIG. 3 shows an X-ray imaging system comprising a robotic base unit supporting a rotatable arm via a joint enabling rotation of the rotatable arm unrestricted by cabling, according to invention principles.

FIG. 3 shows X-ray imaging system 100 usable in medical interventional procedures, according to invention principles, comprising a robotic base unit 40 supporting a rotatable arm (e.g., C-arm) 45 via joints and pivots 70 enabling rotation of the rotatable arm about patient table 48 unrestricted by cabling. A robotic base 40 advantageously drives C-arm 45 through multiple joints and pivots 70 (four joints are shown in FIG. 3) in three axes of motion including rotation and supporting a full range of motion about a patient positioned on patient table 48. The joints or pivots 70 enable 360 degree rotation of rotatable C-arm 45 in at least one plane. System 100 is an interventional X-ray imaging system with electrical low and high voltage power being integrally conveyed within the stand 40 and C-arm 45 through contact rings in joints and pivots 70, for example. Image data as well as data and control signals are communicated via wireless communication between system image processing and control unit 42 and wireless X-ray detector image data and control interface 44 on C-arm 45. The C-arm 45 devices also include X-ray emission tube, collimator and SID (source-imager-distance) drive unit 47 including mechanical drives for SID, detector and collimator rotation. The wireless X-ray detector in unit 44 does not require cooling in this embodiment.

Figure 7:
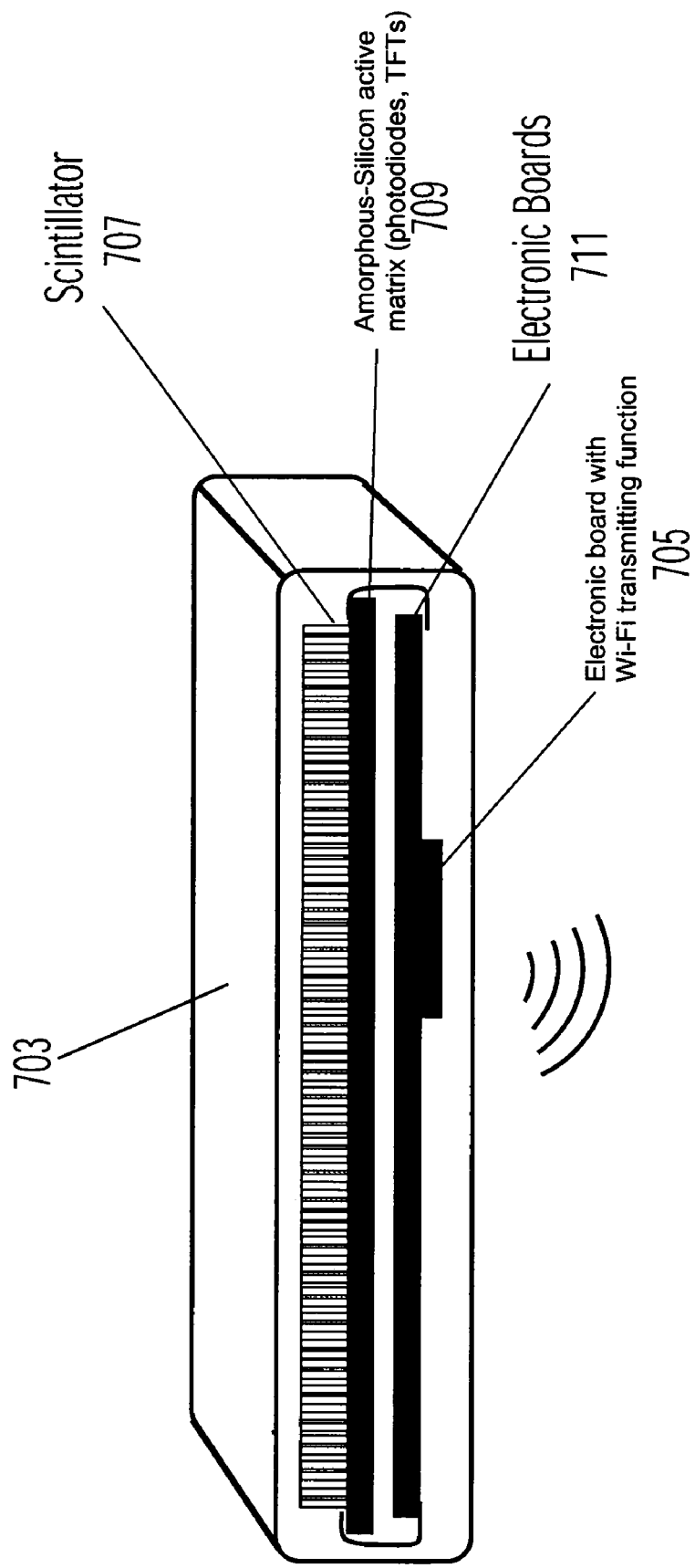
FIG. 7 shows a wireless X-ray detector photodiode matrix with high-speed W-Fi (or other broadband) connection for real-time signal and image data transmission, according to invention principles.

FIG. 7 shows wireless X-ray detector photodiode matrix 709 in unit 703 used in interface 44 (FIG. 3) communicating via high-speed W-Fi (or other broadband) connection provided by electronics 705 and 711 for real-time signal and image data transmission to unit 42. Wireless X-ray detector unit 703 supports high frame-rate X-ray image data acquisition and transmission applications (for example up to 60-100 frames per second). Detector photodiode matrix 709 comprises an integrating detector based on a-Si (amorphous silicon) active matrix and a CsI (cesium iodide) scintillator 707.

Rotatable C-arm 45 of FIG. 3 includes X-ray radiation emitting device 47 located towards one end of rotatable arm C-arm 45 and X-ray detector device 44 located towards the opposite end of rotatable C-arm 45. Detector device 44 acquires X-ray radiation emitted by emitting device 47 having passed through a patient on table 48. Base unit 40 supports rotatable C-arm 45 and includes joints and pivots 70 enabling rotation of rotatable C-arm 45 unrestricted by cabling, about a patient on a support surface (table) 48. Joints and pivots 70 include mating electrical contact surfaces providing electrical power to rotatable C-arm 45 from base unit 40 during rotation of rotatable C-arm 45 unrestricted by cabling. The mating electrical contact surfaces provide, (a) first voltage electrical power to the rotatable arm and (b) different second voltage electrical power to the rotatable arm. Further, the mating electrical contact surfaces are spaced and insulated to maintain electrical isolation between the first and second different voltages. The first voltage electrical power powers a collimator and SID (source-imager-distance) drive unit 47 including mechanical drives for SID, detector and collimator rotation. The second voltage electrical power is a high voltage relative to the first voltage and is for use in providing X-ray emission, for example. A wireless electrical (or optical) signal interface in unit 44 provides electrical signals received from rotatable C-arm 45 to unit 42 (which may be part of base unit 40 or a processing device) during rotation of rotatable C-arm 45 unrestricted by cabling. X-ray imaging system controller 42 controls application of electrical power to rotatable C-arm 45 via base unit 40. In one embodiment, the mating electrical contact surfaces comprise concentric electrical contact rings.

Other embodiments involve different methods of conveying relatively high and low power, relatively high and low voltage, image data, control signals and of providing cooling. The wireless X-ray image detector interface in unit 44 may comprise a Wi-Fi link, WIMAX or other broadband local point-to-point network link. If the X-ray image detector in unit 44 requires cooling, C-arm 45 (and its entire mass) may be used to remove the heat. In one embodiment, rotatable arm C-arm 45 includes a high voltage power supply unit for generating relatively high voltage electrical power using relatively low voltage electrical input power. The relatively high voltage electrical power being for use in providing X-ray emission and the relatively low voltage electrical input power being provided via the mating electrical contact surfaces. In another embodiment, unit 44 comprises a non-cooled detector with an optical data and control signal interface for conveying signals through joints and pivots 70 in robotic stand 40. The X-ray image detector in unit 44 adaptively operates at different frame rates, including 1, 2, and 4 image frames per second (fps) for Digital Subtraction Angiography (DSA) applications or road mapping, 15 fps for fluoroscopy or up to 60-100 fps (or even higher) for three dimensional (3D) anatomical volume image data acquisitions. The X-ray image detector in unit 44 may comprise an integrating detector based on a-Si (amorphous silicon) active matrix and a CsI (cesium iodide) scintillator. Alternately, the detector may be a counting detector and use direct-conversion X-ray materials.

Figure 4:
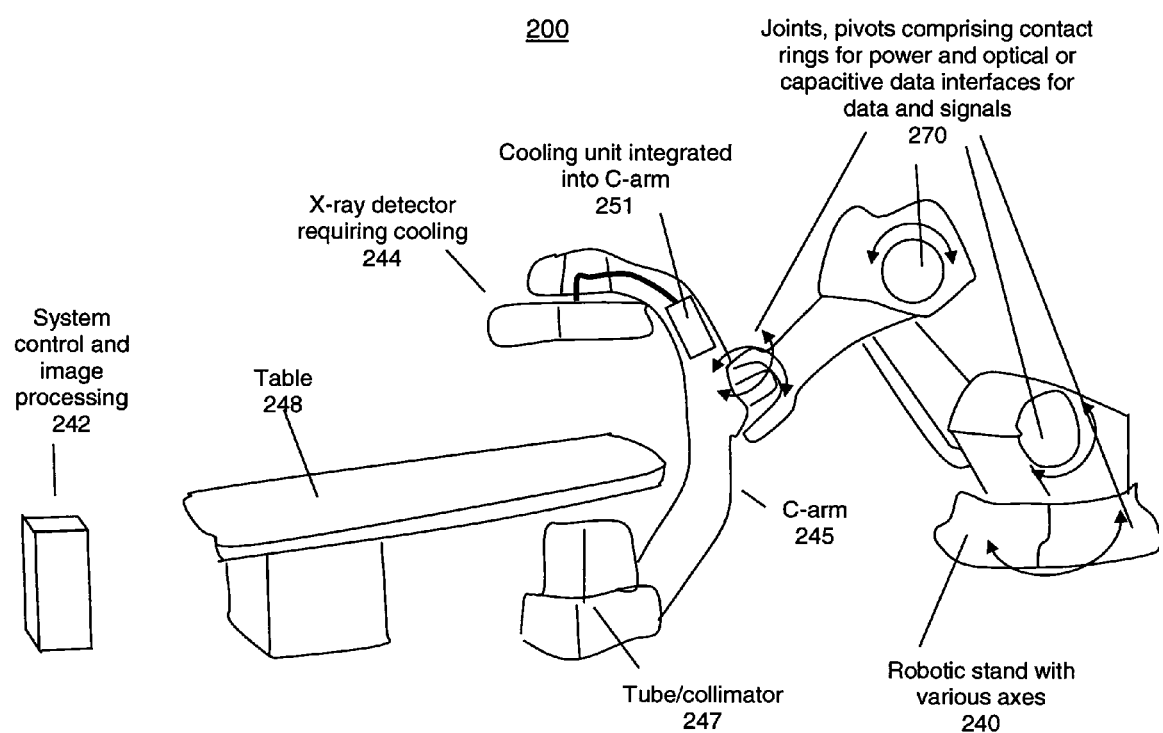
FIG. 4 shows an X-ray imaging system comprising a robotic base unit supporting a rotatable arm with integrated cooling unit and using a joint enabling rotation of the rotatable arm unrestricted by cabling, according to invention principles.

FIG. 4 shows X-ray imaging system 200 comprising robotic base unit 240 supporting rotatable C-arm 245 with integrated cooling unit 251 and using joints and pivots 270 enabling rotation of rotatable C-arm 245 unrestricted by cabling. Imaging system 200 comprises a diagnostic and interventional X-ray imaging system comprising robotic stand 240 without external cables and with high voltage power and low voltage power being integrally conveyed within stand 240 and C-arm 245 through contact rings in joints and pivots 270. Image and control signals including unidirectional and bidirectional data and control signals are transferred via mating electrical contact surfaces or wireless optical or capacitive coupling interfaces in joints and pivots 270, between C-arm 245 and base unit 240 or another device. The X-ray image detector 244 is cooled by cooling unit 251 integrated into C-arm 245. Cooling unit 251 provides device cooling using relatively low voltage electrical input power and the relatively low voltage electrical input power is provided via the mating electrical contact surfaces. Rotatable C-arm 245 includes X-ray radiation emitting device 247 located towards one end of rotatable arm C-arm 245 and X-ray detector device 244 located towards the opposite end of rotatable C-arm 245. Detector device 244 acquires X-ray radiation emitted by emitting device 247 having passed through a patient on table 248. X-ray imaging system controller 242 controls application of electrical power to rotatable C-arm 245 via base unit 240.

Figure 5:
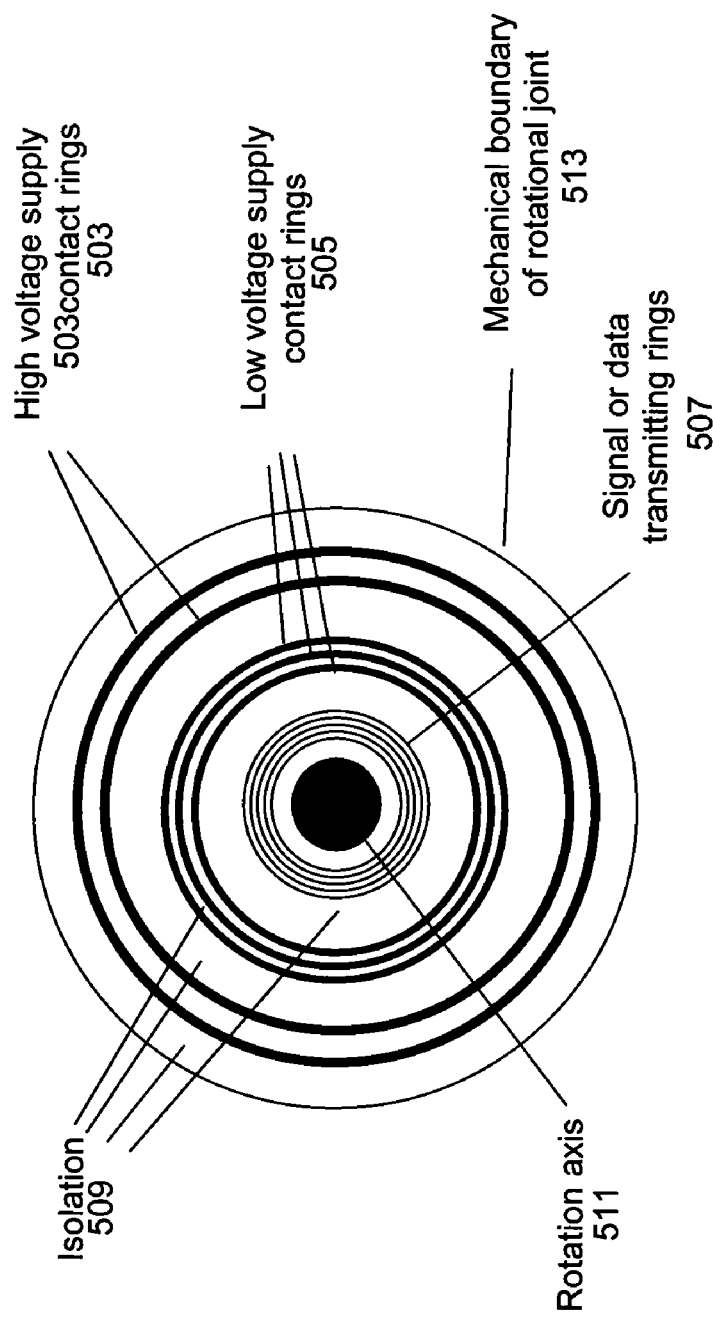
FIG. 5 shows an electrical contact arrangement employed by a joint enabling rotation of an X-ray imaging system rotatable arm unrestricted by cabling, according to invention principles.

FIG. 5 shows an electrical contact arrangement employed by a joint enabling rotation of an X-ray imaging system rotatable arm unrestricted by cabling. The joint allows continuous rotation around central axis 511 within joint boundary 513. Metal contact rings 503 and 505 provide high and low voltage power transmission through a joint, respectively. Metal contact rings 507 provide image data, control data and signal data transmission, through a joint, respectively. The contact rings are isolated from each other by insulated spacing 509.

Figure 6:
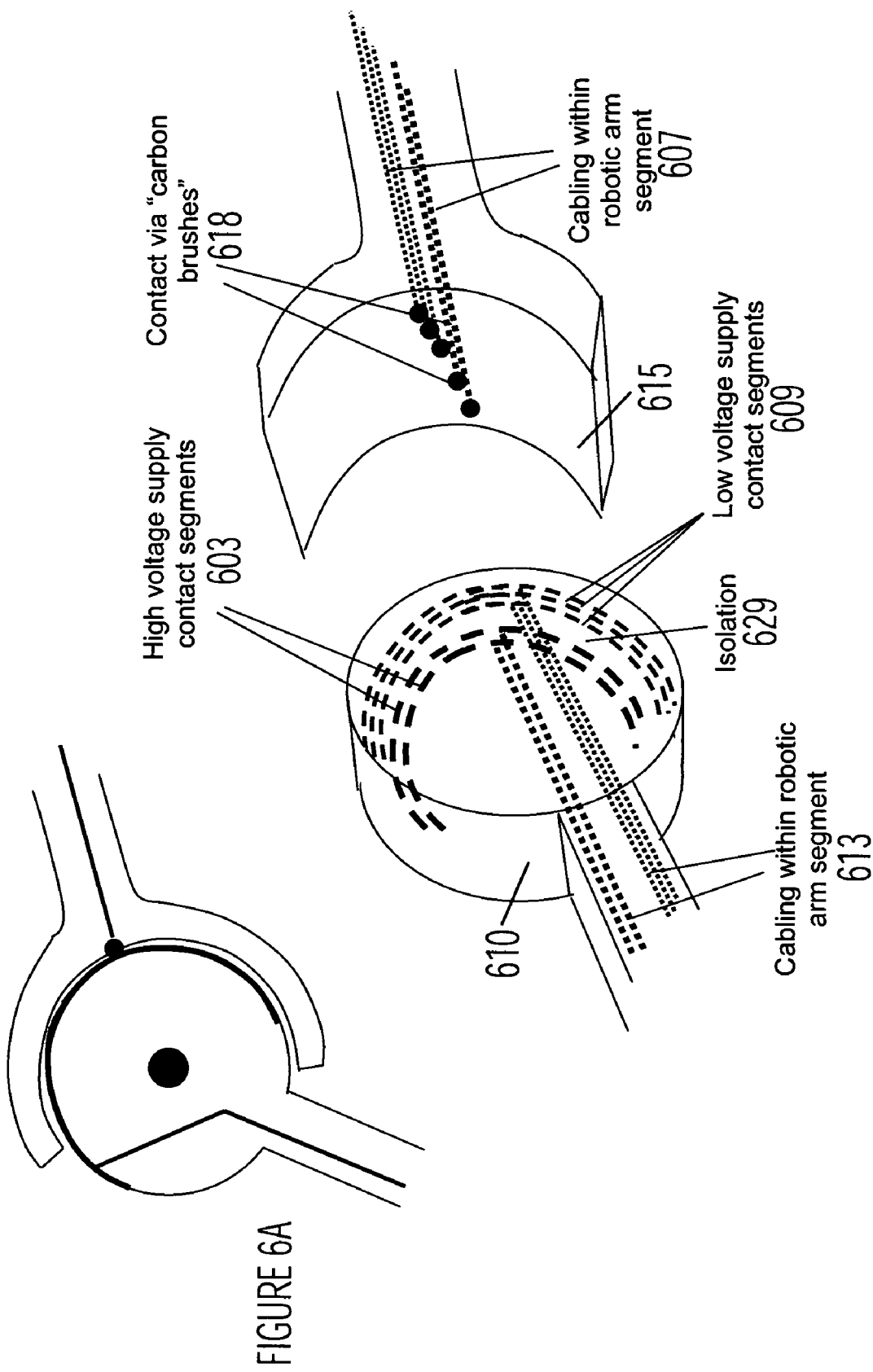
FIGS. 6A and 6B show a knee-type joint with contact segments and carbon or graphite brushes for power transmission enabling rotation of an X-ray imaging system rotatable arm unrestricted by cabling, according to invention principles.

FIGS. 6A and 6B show a knee-type joint with contact segments and carbon or graphite brushes for power transmission enabling rotation of an X-ray imaging system rotatable arm unrestricted by cabling. FIG. 6A shows a two dimensional view showing the joint without cabling. FIG. 6B shows a three dimensional view showing both parts of the joint 610 and 615 in a separated view indicating high voltage contact segments 603 and low voltage contact segments 609. Contact segments 603 and 609 electrically mate with carbon brushes 618. The high and low voltage segments are separated by isolation distance 629. Electrical power is conveyed within robotic arm via cabling 607 and 613.

The systems of FIGS. 1-7 are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, the processes and applications may, in alternative embodiments, be located on one or more (e.g., distributed) processing devices. Any of the functions and steps provided in FIGS. 1-7 may be implemented in hard, software or a combination of both.

What is claimed is:

1. An X-ray imaging system usable in medical interventional procedures, comprising:
   a rotatable arm including an X-ray radiation emitting device located towards one end of said rotatable arm and an X-ray detector device located towards the opposite end of said rotatable arm, said detector device acquiring X-ray radiation emitted by the emitting device and having passed through a patient;
   a base unit supporting said rotatable arm and including a joint or pivot enabling rotation of said rotatable arm unrestricted by cabling, about a patient on a support surface, said joint or pivot including,
   (a) mating electrical contact surfaces providing electrical power to said rotatable arm from said base unit during rotation of said rotatable arm unrestricted by cabling and
   (b) a signal interface for providing electrical signals received from said rotatable arm to at least one of, said base unit and a processing device, during rotation of said rotatable arm unrestricted by cabling; and an X-ray imaging system controller for controlling application of electrical power to said rotatable arm via said base unit.

2. A system according to claim 1, wherein
said mating electrical contact surfaces provide,
(a) first voltage electrical power to said rotatable arm and
(b) different second voltage electrical power to said rotatable arm, said second voltage electrical power being high voltage relative to said first voltage and for use in providing X-ray emission.

3. A system according to claim 2, wherein
said mating electrical contact surfaces are spaced and insulated to maintain electrical isolation between the first and second different voltages.

4. A system according to claim 1, wherein
said mating electrical contact surfaces comprise concentric electrical contact rings.

5. A system according to claim 1, wherein
said signal interface for providing electrical signals received from said rotatable arm comprises mating electrical contact surfaces.

6. A system according to claim 1, wherein
said signal interface for providing electrical signals received from said rotatable arm comprises a wireless electrical signal interface.

7. A system according to claim 1, wherein
said signal interface for providing electrical signals received from said rotatable arm comprises a wireless optical signal interface.

8. A system according to claim 1, wherein
said signal interface for providing electrical signals received from said rotatable arm comprises a wireless capacitive coupling signal interface.

9. A system according to claim 1, wherein
said signal interface bidirectionally exchanges electrical signals between said rotatable arm and said base unit.

10. A system according to claim 1, wherein
said rotatable arm includes a high voltage power supply unit for generating relatively high voltage electrical power using relatively low voltage electrical input power, said relatively high voltage electrical power being for use in providing X-ray emission and said relatively low voltage electrical input power being provided via said mating electrical contact surfaces.

11. A system according to claim 1, wherein
said rotatable arm includes a cooling unit for providing device cooling using relatively low voltage electrical input power, said relatively low voltage electrical input power being provided via said mating electrical contact surfaces.

12. A system according to claim 1, wherein
said joint or pivot enables 360 degree rotation of said rotatable arm in at least one plane.

13. A system according to claim 1, wherein
said rotatable arm comprises a rotatable C-arm.

14. An X-ray imaging system usable in medical interventional procedures, comprising:
a rotatable arm including an X-ray radiation emitting device located towards one end of said rotatable arm and an X-ray detector device located towards the opposite end of said rotatable arm, said detector device acquiring X-ray radiation emitted by the emitting device and having passed through a patient;
a base unit supporting said rotatable arm and including a joint or pivot enabling rotation of said rotatable arm unrestricted by cabling, about a patient on a support surface, said joint including,
(a) mating electrical contact surfaces providing electrical power to said rotatable arm from said base unit during rotation of said rotatable arm unrestricted by cabling and
(b) a wireless electrical signal interface for providing electrical signals received from said rotatable arm to at least one of, said base unit and a processing device, during rotation of said rotatable arm unrestricted by cabling; and
an X-ray imaging system controller for controlling application of electrical power to said rotatable arm via said base unit.

15. A system according to claim 14, wherein
said mating electrical contact surfaces provide,
(a) first voltage electrical power to said rotatable arm and
(b) different second voltage electrical power to said rotatable arm, said second voltage electrical power being high voltage relative to said first voltage and for use in providing X-ray emission.

16. A system according to claim 15, wherein
said first voltage electrical power powers a collimator and SID (source-imager-distance) drive unit including mechanical drives for SID, detector and collimator rotation.

17. A system according to claim 15, wherein
said mating electrical contact surfaces are spaced and insulated to maintain electrical isolation between the first and second different voltages.

18. A system according to claim 14, wherein
said wireless electrical signal interface comprises at least one of, (a) a Wi-Fi link, (b) a WIMAX link and (c) another broadband local point-to-point network link.

* * * * *